United States Patent
Miyairi et al.

(10) Patent No.: US 10,365,201 B2
(45) Date of Patent: Jul. 30, 2019

(54) PRESSURE LOSS ANALYSIS METHOD, A NON-TRANSITORY COMPUTER READABLE MEDIUM, AND A PRESSURE LOSS ANALYSIS APPARATUS FOR ANALYZING PRESSURE LOSS IN A HONEYCOMB STRUCTURE

(71) Applicant: NGK INSULATORS, LTD., Nagoya (JP)

(72) Inventors: Yukio Miyairi, Nagoya (JP); Satoshi Sakashita, Nagoya (JP); Kazuya Mori, Nagoya (JP); Naoki Yoshida, Nagoya (JP); Shingo Sokawa, Nagoya (JP); Kenji Suzuki, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 89 days.

(21) Appl. No.: 15/258,246

(22) Filed: Sep. 7, 2016

(65) Prior Publication Data
US 2017/0102312 A1 Apr. 13, 2017

(30) Foreign Application Priority Data
Oct. 13, 2015 (JP) .................... 2015-202114

(51) Int. Cl.
*G01N 15/08* (2006.01)
*B01D 46/24* (2006.01)

(52) U.S. Cl.
CPC ......... *G01N 15/082* (2013.01); *B01D 46/247* (2013.01); *B01D 46/2459* (2013.01); *B01D 2273/18* (2013.01); *G01N 2015/084* (2013.01)

(58) Field of Classification Search
CPC .... G01N 15/082; G01N 15/0826; G01N 3/12; G01N 2015/084; B01D 46/2459; B01D 46/247; B01D 2273/18; F01N 3/02; F01N 3/0222; A67G 1/00; E21B 49/00; E21B 47/00
See application file for complete search history.

(56) References Cited

U.S. PATENT DOCUMENTS

| | | | |
|---|---|---|---|
| 2003/0124037 A1* | 7/2003 | Voss | B01D 53/864 422/177 |
| 2004/0079631 A1* | 4/2004 | Birckigt | B01D 53/92 204/164 |

FOREIGN PATENT DOCUMENTS

JP  2005-337086 A1  12/2005

OTHER PUBLICATIONS

S. Hashimoto et al., "SiC and Cordierite Diesel Particulate Filters Designed for Low Pressure Drop and Catalyzed, Uncatalyzed Systems," SAE Technical Paper Series, 2002-01-0322, Mar. 4, 2002.

* cited by examiner

*Primary Examiner* — Lisa M Caputo
*Assistant Examiner* — Nigel H Plumb
(74) *Attorney, Agent, or Firm* — Burr & Brown, PLLC

(57) ABSTRACT

A CPU of an analysis apparatus performs a fluid analysis and derives transient distribution information that represents an accumulation distribution of a particulate layer on an inflow-side inner circumferential surface of a honeycomb structure at a time point after a short time interval Δt (step S130). The CPU then repeatedly performs a fluid analysis by taking into account the transient distribution information derived previous time to repeatedly derive transient distribution information (steps S130 to S150) and then derives post-transient-analysis distribution information that represents the accumulation distribution of the particulate layer at a later time point (step S160).

7 Claims, 8 Drawing Sheets

PRESSURE LOSS ANALYSIS METHOD, A NON-TRANSITORY COMPUTER READABLE MEDIUM, AND A PRESSURE LOSS ANALYSIS APPARATUS FOR ANALYZING PRESSURE LOSS IN A HONEYCOMB STRUCTURE

BACKGROUND OF THE INVENTION

1. Field of the Invention

The present invention relates to a pressure loss analysis method, a program for executing the pressure loss analysis method, and a pressure loss analysis apparatus.

2. Description of the Related Art

Honeycomb structures including partition walls that form a plurality of cells serving as flow paths for a fluid are known so far (for example, PTL 1). Honeycomb structures are used to clean exhaust gas from internal combustion engines, for example, automobile engines, and prediction of a pressure loss that occurs when exhaust gas passes through a honeycomb structure is carried out. In PTL 1 for example, a pressure loss is predicted by virtually separating the factors that cause the pressure loss in a honeycomb structure into four kinds of factors on the basis of an internal pressure distribution determined using computational fluid analysis and by adding the values of the pressure loss predicted for the four kinds of factors together. PTL 1 states that a pressure loss can be accurately predicted in this way.

PTL 1 gives an example of a pressure loss prediction method for a catalytic converter that converts harmful substances in gas to harmless substances by just allowing the gas to pass through open flow paths of cells of a honeycomb structure to bring the gas into contact with a catalyst that coats the surfaces of the cell partition walls. Other exemplary usages of a honeycomb structure include the use of a honeycomb structure in which inlets and outlets of cells are alternately plugged such that gas passes through cell partition walls in order to filter particulate matter contained in engine emissions and exhaust gas from other combustion devices and the use of such a structure in order to filter solid particulates contained in a liquid, such as water. In this filtering usage, pressure loss prediction in a state where particulate matter has accumulated is essential because resistance of each partition wall against the passing gas increases due to accumulation of particulate matter on the partition wall. In conventional pressure loss prediction methods for the particulate matter accumulation state, the analysis is performed on the assumption that particulate matter accumulates on the surfaces of the partition walls in a uniform thickness t (t=M/S, where M denotes the total amount of particulate matter and S denotes the total surface area of partition walls of inlet cells) as in NPL 1, for example.

CITATION LIST

Patent Literature

[PTL 1] Japanese Unexamined Patent Application Publication No. 2005-337086

Non Patent Literature

[NPL 1] SAE TECHNICAL PAPER SERIES, 2002-01-0322

SUMMARY OF THE INVENTION

However, PTL 1 and NPL 1 do not take into account an accumulation distribution of particulate matter, and no method for accurately simulating how particulate matter accumulates at each part of the partition portions when a fluid flows inside a honeycomb structure is known.

The present invention has been made to overcome such an issue, and a main object thereof is to analyze a pressure loss by more accurately simulating the accumulation state of particulate matter.

The present invention employs the following measures to achieve the main object described above.

A pressure loss analysis method of the present invention is a method for analyzing a pressure loss in a honeycomb structure for a case where a fluid flows inside the honeycomb structure, the honeycomb structure including porous partition portions that form a plurality of inflow-side cells and a plurality of outflow-side cells, the pressure loss analysis method comprises:

a transient analysis step of repeatedly performing a particulate-layer-distribution deriving process, in which transient distribution information that represents an accumulation distribution of a particulate layer on an inflow-side inner circumferential surface is derived by performing a fluid analysis for the case where the fluid flows inside the honeycomb structure on the basis of object information that simulates the honeycomb structure with a plurality of mesh portions and by deriving, for each of the mesh portions corresponding to the inflow-side inner circumferential surface that is an inner circumferential surface of each of the inflow-side cells among a surface of the partition portion, a state of the particulate layer, which is a layer in which particulate matter contained in the fluid has accumulated, at a time point after a short time interval, and of deriving post-transient-analysis distribution information that represents the accumulation distribution at a time point after the particulate-layer-distribution deriving process has been performed a plurality of times, by performing the fluid analysis during the particulate-layer-distribution deriving process performed for the second and following times while taking into account the transient distribution information derived in an immediately preceding particulate-layer-distribution deriving process; and a pressure loss deriving step of deriving a pressure loss for the case where the fluid flows inside the honeycomb structure, by performing a fluid analysis on the basis of the object information and the post-transient-analysis distribution information.

In this pressure loss analysis method, transient distribution information that represents an accumulation distribution of a particulate layer on an inflow-side inner circumferential surface of a honeycomb structure at a time point after a short time interval is derived by performing a fluid analysis. Then, transient distribution information is repeatedly derived by performing a fluid analysis while taking into account the transient distribution information derived previous time, and consequently post-transient-analysis distribution information that represents the accumulation distribution of the particulate layer at a later time point is derived. By repeatedly analyzing the accumulation distribution of the particulate layer at each time point after the short time interval in this way, a transient change in the accumulation distribution of the particulate layer over time can be accurately analyzed. Thus, the accumulation state (accumulation distribution) of the particulate layer at a time point after the short time interval has passed a plurality of times is accurately simulated by the post-transient-analysis distribution information. For example, the state closer to the actual accumulation state of the particulate layer can be simulated compared with the case of simulating a state where the particulate layer has evenly accumulated at every position on the inflow-side inner circumferential surface (state where the particulate layer is distributed evenly). Since a pressure loss for the case where the fluid flows inside the honeycomb structure is derived on the basis of this post-transient-analysis distribution information, the pressure loss can be analyzed by more accurately simulating the accumulation state of the particulate matter.

In the pressure loss analysis method according to the present invention, during the particulate-layer-distribution deriving process, the transient distribution information may be derived on the basis of information regarding a concentration of the particulate matter in the fluid and information regarding a flow rate of the fluid that flows into each of the mesh portions corresponding to the inflow-side inner circumferential surface, the information regarding the flow rate being a value derived through the fluid analysis performed during the particulate-layer-distribution deriving process. Here, the higher the concentration of the particulate matter in the fluid and the larger the flow rate of the fluid that flows through the inflow-side inner circumferential surface, the more the particulate matter accumulates. Accordingly, the transient distribution information can be appropriately derived by using the information regarding the concentration of the particulate matter in the fluid and the information regarding the flow rate of the fluid. That is, the accumulation state of the particulate layer can be appropriately simulated.

In the pressure loss analysis method according to the present invention, each of the transient distribution information and the post-transient-analysis distribution information may be information including at least one of a distribution of thickness of the particulate layer, a distribution of permeability of the particulate layer, and a distribution of flow resistance of the particulate layer. Since thickness, permeability, and flow resistance are information that influences a pressure loss that occurs when the fluid passes through the particulate layer, they are suitable as information representing the accumulation distribution of the particulate layer (the transient distribution information and the post-transient-analysis distribution information).

In the pressure loss analysis method according to the present invention, in the transient analysis step, the particulate-layer-distribution deriving process may be performed repeatedly until at least one of a total amount of the particulate matter that has accumulated on the inflow-side inner circumferential surface reaches a predetermined target amount or the sum of the short time intervals reaches a predetermined target period. With such a configuration, the accumulation state of the particulate layer in a state for which analysis of the pressure loss is desired (state where the target amount or the target period has been reached) can be simulated relatively easily, and the pressure loss in that state can be derived easily.

In the pressure loss analysis method according to the present invention, the object information may be information that simulates the honeycomb structure having an area ratio A of 15% or greater. The area ratio A is a ratio of an inflow-inflow facing area to an area of the inflow-side inner circumferential surface. The inflow-inflow facing area is an area of a portion of the inflow-side inner circumferential surface facing the inflow-side inner circumferential surface of another inflow-side cell. When a fluid containing particulate matter passes through the honeycomb structure, the particulate matter is unlikely to accumulate evenly on the inflow-side inner circumferential surface in the honeycomb structure having the area ratio A of 15% or greater. Accordingly, the value of the pressure loss derived by simulating the state where the particulate layer is evenly distributed tends to deviate from the actually measured value of the pressure loss measured using the honeycomb structure in which the same amount of particulate matter has accumulated. That is, the accuracy of the pressure loss analysis tends to decrease. In contrast, a deviation of the value derived using the pressure loss analysis method according to the present invention from the actually measured value is small also for the honeycomb structure having the area ratio A of 15% or greater, and thus the pressure loss analysis can be performed more accurately. Therefore, it is beneficial to employ the present invention when the pressure loss analysis is performed for the honeycomb structure having the area ratio A of 15% or greater.

A program according to the present invention is a program causing one or a plurality of computers to perform the individual steps of the above-described pressure loss analysis method. This program may be stored on a computer-readable recording medium (e.g., a hard disk, a ROM, an FD, a CD, a DVD, or the like), distributed from a certain computer to another computer via a transmission medium (network such as the Internet or a LAN), or transmitted and received in any other way. Since the individual steps of the above-described pressure loss analysis method are performed when this program is executed by one computer or a plurality of computers by distributing processes to the respective computers, advantageous effects similar to those of the method are obtained.

A pressure loss analysis apparatus of the present invention is an apparatus for analyzing a pressure loss in a honeycomb structure for a case where a fluid flows inside the honeycomb structure, the honeycomb structure including porous partition portions that form a plurality of inflow-side cells and a plurality of outflow-side cells, the pressure loss analysis apparatus comprises:

transient analysis device for repeatedly performing a particulate-layer-distribution deriving process, in which transient distribution information that represents an accumulation distribution of a particulate layer on an inflow-side inner circumferential surface is derived by performing a fluid analysis for the case where the fluid flows inside the honeycomb structure on the basis of object information that simulates the honeycomb structure with a plurality of mesh portions and by deriving, for each of the mesh portions corresponding to the inflow-side inner circumferential surface that is an inner circumferential surface of each of the inflow-side cells among a surface of the partition portion, a state of the particulate layer, which is a layer in which particulate matter contained in the fluid has accumulated, at a time point after a short time interval, and for deriving post-transient-analysis distribution information that represents the accumulation distribution at a time point after the particulate-layer-distribution deriving process has been performed a plurality of times, by performing the fluid analysis during the particulate-layer-distribution deriving process performed for the second and following times while taking into account the transient distribution information derived in an immediately preceding particulate-layer-distribution deriving process; and pressure loss deriving device for deriving a pressure loss for the case where the fluid flows inside the honeycomb structure, by performing a fluid analysis on the basis of the object information and the post-transient-analysis distribution information.

This pressure loss analysis apparatus is capable of analyzing a pressure loss by more accurately simulating the accumulation state of particulate matter, like the pressure loss analysis method described above. Note that each device of this pressure loss analysis apparatus may perform an additional operation or an additional device may be added to this pressure loss analysis apparatus so that the above-described various embodiments of the pressure loss analysis method are implemented.

DETAILED DESCRIPTION OF THE INVENTION

Figure 1:
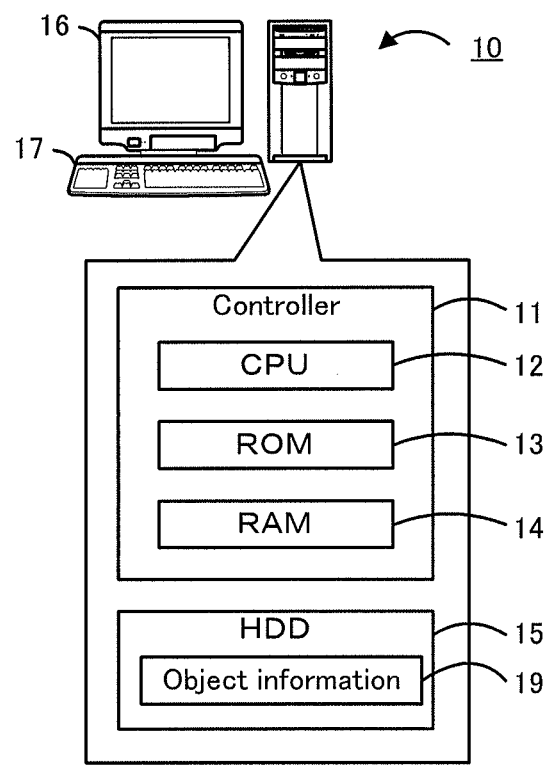
FIG. 1 is a diagram illustrating a schematic configuration of an analysis apparatus 10.

An embodiment of the present invention will be described next by using the drawings. FIG. 1 is a diagram illustrating a schematic configuration of an analysis apparatus 10, which is an embodiment of the present invention. This analysis apparatus 10 is implemented as a computer, such as a personal computer, and includes a controller 11 and an HDD 15. The controller 11 includes a CPU 12 that performs various processes, a ROM 13 that stores programs for the various processes and the like, and a RAM 14 that temporarily stores data, for example. The HDD 15 is a large-capacity memory that stores various processing programs, such as an analysis process program, and various kinds of data used in the analysis process. The analysis apparatus 10 also includes a display 16 that displays various kinds of information on its screen, and an input device 17 such as a mouse and keyboard used by a user to input various kinds of instructions. Although details will be described later, the HDD 15 stores object information 19 and the like. The object information 19 is information that simulates an object subjected to an analysis. This analysis apparatus 10 analyzes a pressure loss that occurs when a fluid flows inside an object simulated by the object information 19, on the basis of the object information 19 and the like stored on the HDD 15.

Figure 2:
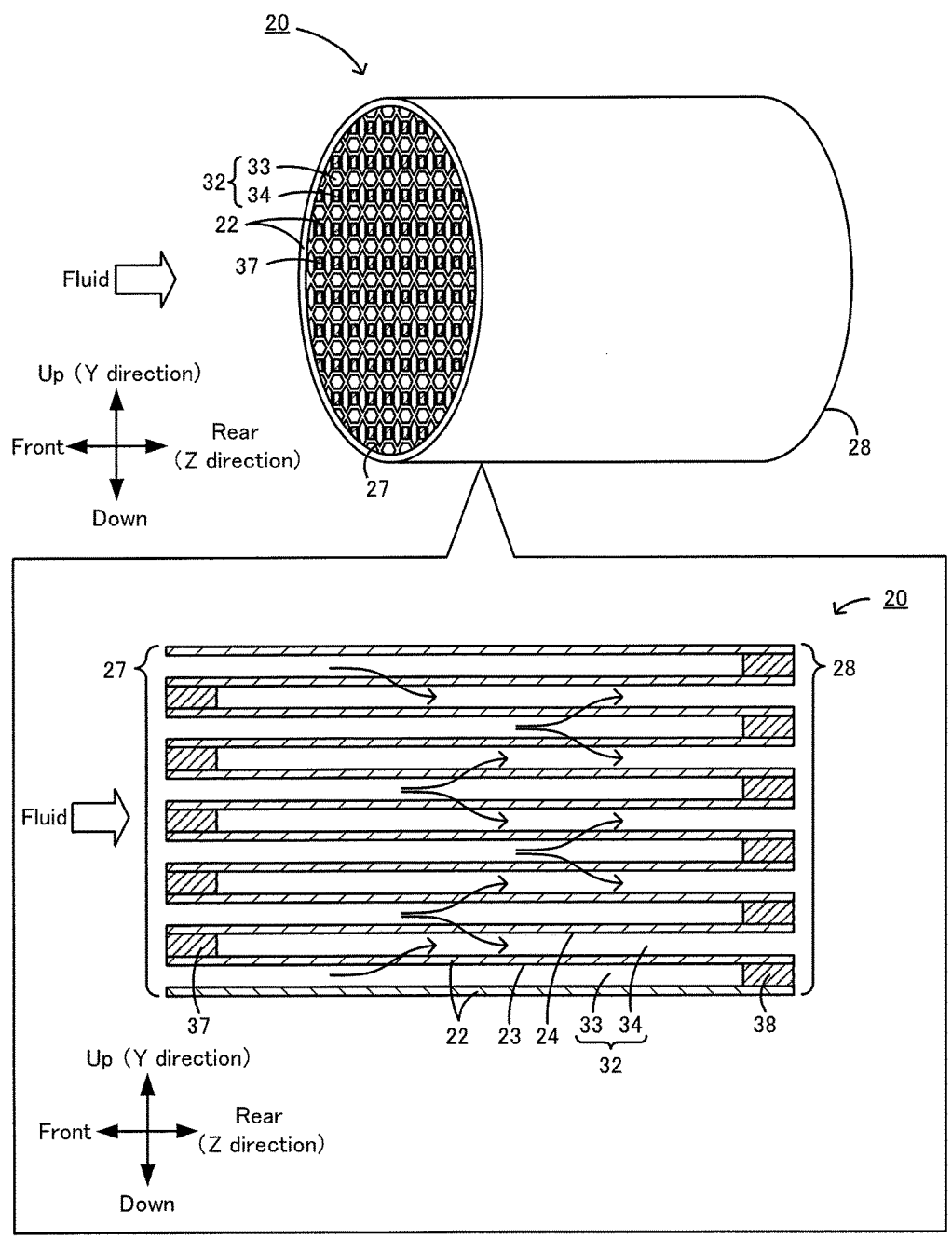
FIG. 2 is an explanatory diagram illustrating an example of a schematic configuration of a honeycomb structure 20.
Figure 3:
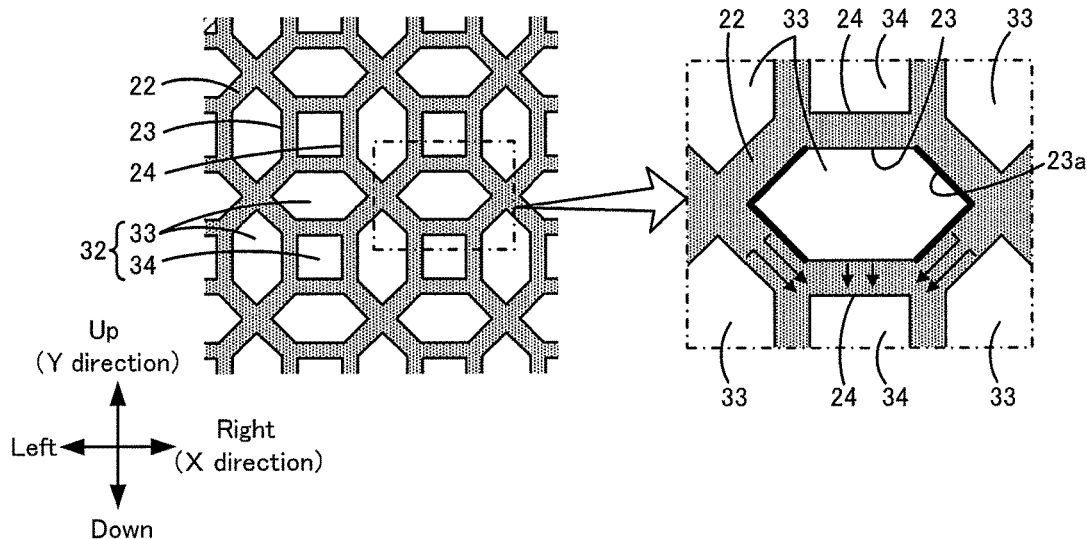
FIG. 3 is an explanatory diagram of partition portions 22 and cells 32 of the honeycomb structure 20.

Now, an object subjected to an analysis by the analysis apparatus 10 will be described. FIG. 2 is an explanatory diagram illustrating an example of a schematic configuration of a honeycomb structure 20, which is an example of an object subjected to an analysis. FIG. 3 is an explanatory diagram of partition portions 22 and cells 32 of the honeycomb structure 20. Note that the up-down direction and the front-rear direction are assumed as illustrated in FIG. 2 in this embodiment. In addition, a direction perpendicular to the up-down direction and the front-rear direction is assumed as the right-left direction (see FIG. 3). Further, it is assumed that the right direction is the X-direction (positive direction on the X axis), the up direction is the Y direction (positive direction on the Y axis), and the rear direction is the Z direction (positive direction on the Z axis). The honeycomb structure 20 is used as a diesel particulate filter (DPF) having a function of filtering particulate matter (PM) contained in exhaust gas from a diesel engine, for example.

As illustrated in FIG. 2, the honeycomb structure 20 includes porous partition portions 22 that form a plurality of cells 32 serving as flow paths for a fluid (exhaust gas), front-side plugging portions 37 that plug one end of some of the cells 32, and rear-side plugging portions 38 that plug one end of some of the cells 32. The external shape of the honeycomb structure 20 may be, but not limited to, circular cylindrical, quadrangular cylindrical, elliptical cylindrical, or hexagonal cylindrical, for example. The external shape is assumed to be circular cylindrical in this embodiment. As illustrated in FIG. 3, the partition portions 22 form a plurality of inflow-side cells 33 and a plurality of outflow-side cells 34, both of which constitute the plurality of cells 32. The inflow-side cells 33 have a hexagonal cross-section. One end (on a front-end-surface-27 side) of the inflow-side cells 33 is open, whereas the other end (on a rear-end-surface-28 side) thereof is plugged with the rear-side plugging portion 38. The outflow-side cells 34 have a quadrangular cross-section. One end of the outflow-side cells 34 is plugged with the front-side plugging portion 37, whereas the other end thereof is open. An inner circumferential surface of each of the inflow-side cells 33 among the surface of the partition portions 22 is referred to as an inflow-side inner circumferential surface 23. An inner circumferential surface of each of the outflow-side cells 34 among the surface of the partition portions 22 is referred to as an outflow-side inner circumferential surface 24. The inflow-side cells 33 are adjacent to and on the right, left, upper, and lower sides of each of the outflow-side cells 34. Surfaces extending in the X direction and surfaces extending in the Y direction among the inflow-side inner circumferential surfaces 23 face the outflow-side inner circumferential surfaces 24. In addition, surfaces of the inflow-side inner circumferential surfaces 23 of the plurality of inflow-side cells 33 inclined from the X direction and the Y direction face each other. A portion of the inflow-side inner circumferential surface 23 that faces the inflow-side inner circumferential surface 23 of another inflow-side cell 33 (but does not face the outflow-side inner circumferential surface 24) is referred to as an inflow-inflow facing surface 23a. In an enlarged view on the right in FIG. 3, the inflow-inflow facing surface 23a is represented by a thick line among the inflow-side inner circumferential surface 23 of the inflow-side cell 33 located at the center. In this honeycomb structure 20, when a fluid flows from the front side, the fluid flows into the inflow-side cells 33 from the inlet side (a front end surface 27), passes through the partition portions 22 from the inflow-side cells 33 and flows into the outflow-side cells 34, and flows out from the outlet side (a rear end surface 28) of the outflow-side cells 34 to the rear side. Note that the fluid that flows into portions of the inflow-side inner circumferential surface 23 other than the inflow-inflow facing surface 23a mainly passes through the partition portion 22 toward the outflow-side inner circumferential surface 24, and flows out to the outflow-side cell 34 as indicated by arrows in the enlarged view on the right side in FIG. 3. In addition, the fluid that flows into the inflow-inflow facing surface 23a flows out to the outflow-side cell 34 after changing its flow direction at the partition portion 22 together with the flow from its opposing inflow-inflow facing surface 23a. As described above, the flow of the fluid that has passed through the inflow-inflow facing surface 23a is different from the flow of the fluid that has passed through the other portion of the inflow-side inner circumferential surface 23 of the inflow-side cell 33 in the honeycomb structure 20. Note that when a fluid flows through the inflow-side inner circumferential surface 23, particulate matter contained in the fluid is collected by the partition portions 22 and accumulates on the inflow-side inner circumferential surface 23 because the particulate matter cannot pass through the partition portions 22. In addition, the honeycomb structure 20 has an area ratio A of 15% or greater. The area ratio A is a ratio of an inflow-inflow facing area to an area of the inflow-side inner circumferential surface 23, and the inflow-inflow facing area is an area of the inflow-inflow facing surface 23a. The area ratio A according to this embodiment is equal to a ratio of the sum of lengths of sides inclined from the X direction and the Y direction (four sides denoted by thick lines in the enlarged view on the right side in FIG. 3) of the hexagonal cross-section of one inflow-side cell 33 to the sum of lengths of sides (six sides) of the hexagonal cross-section of the inflow-side cell 33. Note that since the external shape of the honeycomb structure 20 is circular cylindrical, the inflow-side cells 33 having a shape different from that of the other inflow-side cells 33 are located near the periphery of the honeycomb structure 20. However, the area ratio A is assumed to be a value derived based on the smallest unit (one inflow-side cell 33 in this embodiment) of an iterative structure of the inflow-side cells 33 without taking into account such an exceptional shape of some of the inflow-side cells 33.

Figure 4:
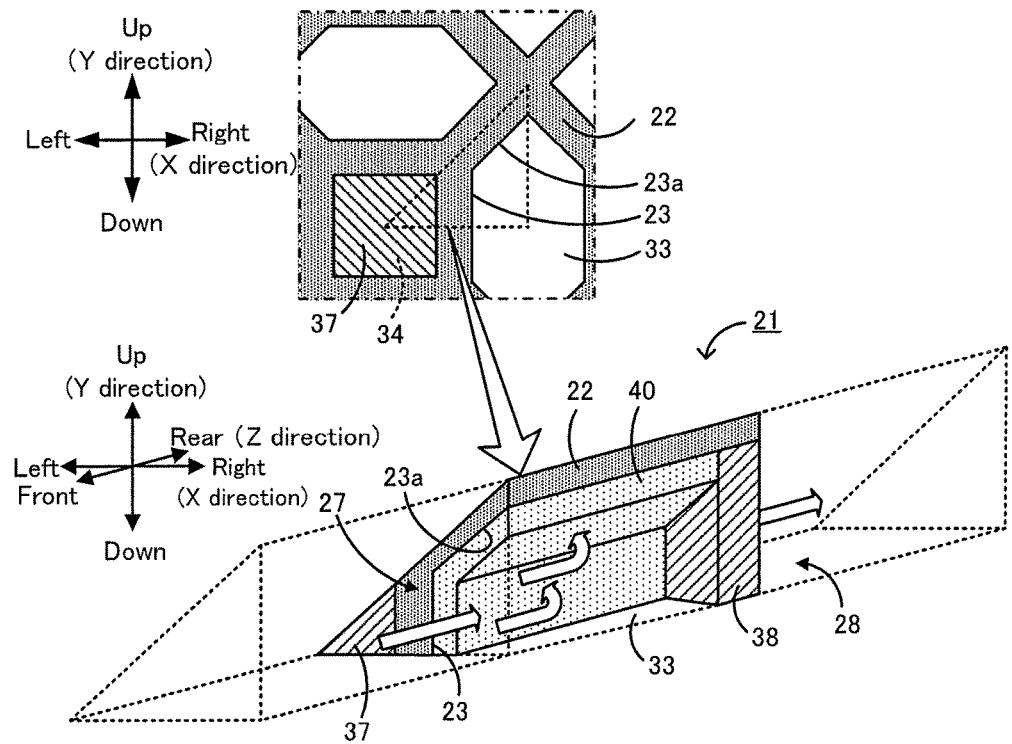
FIG. 4 is a conceptual diagram of a model 21 of the honeycomb structure 20 simulated by object information 19.

The object information 19 stored on the HDD 15 of the analysis apparatus 10 is information that simulates the honeycomb structure 20 illustrated in FIGS. 2 and 3 by using a plurality of mesh portions. FIG. 4 is a conceptual diagram of a model 21 of the honeycomb structure 20 simulated by the object information 19. In this embodiment, the object information 19 is information that simulates the model 21 representing the shape of the smallest unit of the iterative structure of the honeycomb structure 20. An upper portion of FIG. 4 is a partially enlarged view of the front end surface 27 of the honeycomb structure 20. A portion within a dotted line triangular frame denotes the smallest unit of the iterative structure of the honeycomb structure 20. As illustrated in a lower portion of FIG. 4, the model 21 represents the structure of a portion from the front end surface 27 to the rear end surface 28 (triangular-cylindrical portion) within the dotted-line frame illustrated in the upper portion of FIG. 4 extracted from the honeycomb structure 20. The model 21 includes one quarter of the inflow-side cell 33 and one eighth of the outflow-side cell 34 at the cross section along the X-Y plane. In addition, the model 21 may include a space on the front side of the front end surface 27 or a space on the rear side of the rear end surface 28. In the lower portion of FIG. 4, the outflow-side cell 34 in the model 21 is not illustrated; only the front-side plugging portion 37 is illustrated. In the lower portion of FIG. 4, a particulate layer 40, which is a layer formed as a result of particulate matter contained in a fluid accumulating on the inflow-side inner circumferential surface 23, is also illustrated. Note that the object information 19 yet to be subjected to an analysis process (described later) simulates a state where the particulate layer 40 has not yet accumulated on the inflow-side inner circumferential surface 23. Further, in the lower portion of FIG. 4, open arrows indicate the flow of the fluid that flows from the front end surface 27, the flow of the fluid that flows from the inflow-side cell 33 to the partition portion 22 (the inflow-side inner circumferential surface 23), and the flow of the fluid that flows from the rear end surface (the outflow-side cell 34). Each side of the dotted-line triangular frame in the upper portion of FIG. 4 or the periphery of the triangular column of the model 21 corresponds to a structural symmetry plane of of the honeycomb structure 20. By configuring the object information 19 to be information that simulates the smallest unit (the model 21) of the iterative structure of the honeycomb structure 20 in this way, a decrease in the accuracy of the analysis process (described later) is successfully suppressed and a time taken for the analysis process is successfully reduced. Note that the object information 19 is not limited to the above-described information and may be information that simulates the shape including a plurality of smallest units of the iterative structure of the honeycomb structure 20 or information that simulates the whole honeycomb structure 20.

Although the illustration is omitted, the object information 19 is information that simulates the model 21 using a plurality of mesh portions by dividing the model 21 into a plurality of portions in the X, Y, and Z directions. The object information 19 includes, for each of the plurality of mesh portions, type information indicating which part of the honeycomb structure 20 the mesh portion corresponds to and position information (X, Y, and Z coordinates) of the mesh portion, for example. The type information is information indicating which of the space in front of the front end surface 27, the space behind the rear end surface 28, the partition portion 22, the inflow-side cell 33, the outflow-side cell 34, the front-side plugging portion 37, and the rear-side plugging portion 38 the mesh portion corresponds to. How many portions into which the model 21 is divided in the X, Y, and Z directions can be appropriately set by taking into account the required analysis accuracy and the time taken for the analysis (calculation time). In addition, the object information 19 may include various parameters regarding the honeycomb structure 20 used in the analysis process (described later), such as permeability $\alpha w$ [$\mu m^2$] of the partition portion 22 and dimensions (dimensions in the X, Y, and Z directions) of each mesh portion.

The cells 32 and the partition portions 22 having shapes different from those of the smallest unit (the model 21) of the iterative structure are located near the periphery of the honeycomb structure 20. Accordingly, the object information 19 may include information that simulates such shapes different from those of the model 21 separately from the information that simulates the model 21.

Figure 5:
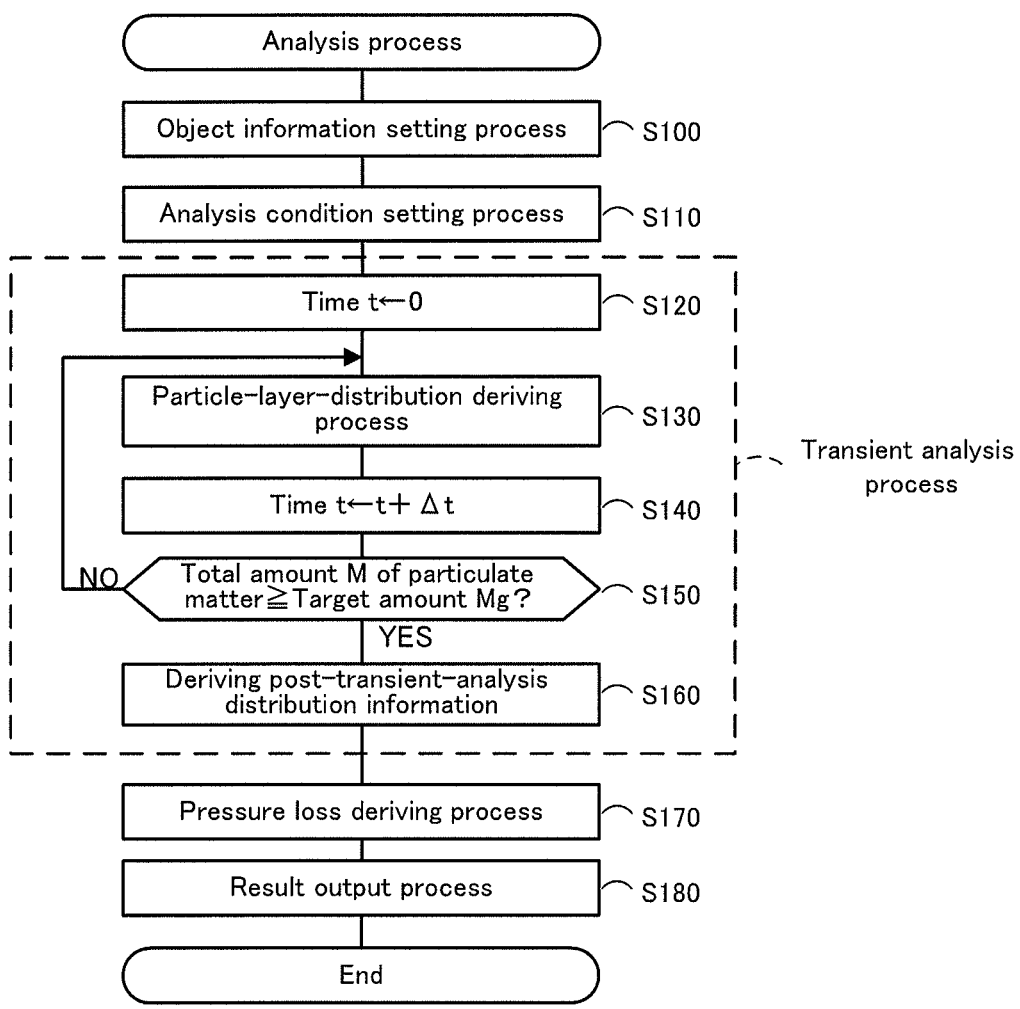
FIG. 5 is a flowchart illustrating an example of an analysis process routine.

The analysis process performed by the analysis apparatus 10 will be described next. The analysis process is a process for analyzing a pressure loss in the honeycomb structure 20 by taking into account a distribution of the particulate layer 40 that has accumulated on the inflow-side inner circumferential surface 23 in response to inflow of a fluid when the fluid flows inside the honeycomb structure 20. FIG. 5 is a flowchart illustrating an example of an analysis process routine. This analysis process routine starts as a result of the CPU 12 executing an analysis process program stored on the HDD 15 upon the user inputting an instruction to perform the analysis process via the input device 17.

Upon the start of the analysis process routine, the CPU 12 performs an object information setting process in which the object information 19 to be subjected to the analysis process is set as the processing target (step S100). In this process, the CPU 12 receives an instruction to perform an analysis based on the object information 19 from the user via the input device 17 and sets the object information 19 as a target subjected to the analysis process on the basis of the received instruction. The object information 19 is stored on the HDD 15 in advance in this embodiment; however, the CPU 12 may obtain the object information 19 from an external recording medium readable by the analysis apparatus 10 or from another computer or the like, store the obtained object information 19 on the HDD 15, and set the stored object information 19 as the analysis target. In addition, the CPU 12 may receive an instruction to modify data of the object information 19 stored on the HDD 15 from the user via the input device 17 and modify the data of the object information 19 on the basis of the received instruction. The following description will be given of the case where the object information 19 that simulates the model 21 described using FIG. 4 is set as the target subjected to the analysis process.

Subsequent to step S100, the CPU 12 performs an analysis condition setting process in which analysis conditions are set (step S110). The CPU 12 sets, for example, information stored on the HDD 15 in advance or information received from the user via the input device 17 as the analysis conditions. In this embodiment, conditions such as fluid inflow conditions, physical property value conditions of the fluid, physical property value conditions of the particulate layer 40, boundary conditions, and a target amount Mg [kg] of particulate matter that has accumulated on the inflow-side inner circumferential surface 23 are set as the analysis conditions. Examples of the fluid inflow conditions include a flow rate Q [$m^3$/s] of a fluid that flows in from the front side of the front end surface 27. Examples of the physical property value conditions of the fluid include a fluid density $\rho g$ [kg/$m^3$], a fluid viscosity $\mu$ [Pa·s], and a concentration of particulate matter in the fluid. The concentration of particulate matter in the fluid may be, for example, a mass/volume concentration Ds1 [kg/$m^3$] or a volume concentration Ds2 [vol %]. Examples of the physical property value conditions of the particulate layer 40 include a permeability $\alpha s$ [$\mu m^2$] of the particulate layer 40 and a density ds [kg/$m^3$] of the particulate layer 40. Examples of the boundary conditions include a fluid pressure Pin [Pa] at the inlet of the model 21 or a fluid pressure Pout [Pa] at the outlet of the model 21. Note that the fluid inflow conditions may change depending on the time t or the position on the X-Y plane. The physical property value conditions of the fluid may change depending on the time t.

Subsequent to step S110, the CPU 12 performs a process (transient analysis process) including steps S120 to S160. Note that the CPU 12 performs the transient analysis process while appropriately reading and obtaining (referring to) the object information 19 and the analysis conditions respectively set (stored on the HDD 15) in steps S100 and S110. Upon the start of the transient analysis process, the CPU 12 first sets time t to the analysis start time (value of 0) (step S120). Then, the CPU 12 performs a fluid analysis for the case where a fluid flows inside the honeycomb structure 20 on the basis of the object information 19 and derives, for each of the mesh portions corresponding to the inflow-side inner circumferential surface 23, a state of the particulate layer 40, which is the accumulation of particulate matter contained in the fluid, after a short time interval $\Delta t$. In this way, the CPU 12 performs a particulate-layer-distribution deriving process for deriving transient distribution information that indicates the state of the particulate layer 40 that has accumulated on the inflow-side inner circumferential surface 23 (step S130). In the particulate-layer-distribution deriving process, any known fluid analysis using the finite element method, the finite volume method, or the like can be used. It is assumed that the finite volume method is used in this embodiment.

In this particulate-layer-distribution deriving process, the CPU 12 assumes each one of the mesh portions of the model 21 included in the object information 19 as a small element in the finite volume method. Then, the CPU 12 derives setting condition values of the fluid analysis, such as a flow resistance Ri [Pa·s/m] between adjacent mesh portions, on the basis of the object information 19 and the analysis conditions respectively set in steps S100 and S110. Then, the CPU 12 derives, for each of the small elements, an equation regarding the flow of the fluid by using the state of the small element at the time t and determines a solution with which the equations hold true for all the small elements (fluid analysis). In this way, the CPU 12 derives a flow velocity Vi [m/s] of the fluid that flows between the adjacent mesh portions, a flow rate Qi [$m^3$/s] of the fluid that flows between the adjacent mesh portions, an absolute pressure Pi [Pa] (total pressure) at each mesh portion, a dynamic pressure [Pa] at each mesh portion, and a static pressure [Pa] at each mesh portion as values regarding the state of each small element (mesh portion) after the short time interval $\Delta t$ from the time t. The CPU 12 stores these derived values on the HDD 15 in association with the corresponding time (the time t+$\Delta t$) and the corresponding mesh portion. Note that the CPU 12 performs the fluid analysis in a state where the particulate layer 40 has not accumulated on the inflow-side inner circumferential surface 23 (without taking into account the particulate layer 40) during the first particulate-layer-distribution deriving process (process performed at the time t=0) of the analysis process.

The CPU 12 then derives, for each of the mesh portions corresponding to the inflow-side inner circumferential surface 23 among the plurality of mesh portions of the model 21, the state of the particulate layer 40 after the short time interval $\Delta t$ on the basis of the values derived through the fluid analysis. Note that the mesh portions corresponding to the inflow-side inner circumferential surface 23 are mesh portions adjacent to mesh portions corresponding to the inflow-side cell 33, among mesh portions corresponding to the partition portions 22. It is assumed that a thickness Ts [$\mu m$] of the particulate layer 40 is derived as the state of the particulate layer 40 in this embodiment. For example, the CPU 12 first sets one of the mesh portions corresponding to the inflow-side inner circumferential surface 23 as a target for which the values are to be derived, and then derives, for the target mesh portion, a product (=a weight Mi [kg] of the particulate matter that has accumulated) of the concentration of the particulate matter in the fluid (e.g., the mass/volume concentration Ds1 [kg/$m^3$] set in step S110), the flow rate Qi [$m^3$/s] of the fluid that flows from the adjacent mesh portion (mesh portion corresponding to the inflow-side cell 33) to the target mesh portion, which is a value derived through the fluid analysis performed this time, and the short time interval $\Delta t$ [s], at a time point after the short time interval (at time t+Δt). The CPU 12 then divides the obtained weight of the particulate matter by the density ds [kg/m³] of the particulate layer 40 set in step S110 and by an area (area of the inflow-side inner circumferential surface 23) of a portion of the target mesh portion facing the inflow-side cell 33 to derive the thickness Ts [μm] of the particulate layer 40. In this way, the CPU 12 derives the state (thickness Ts) of the particulate layer 40 after the short time interval Δt by using the values derived through the fluid analysis on the assumption that an amount of particulate matter corresponding to the flow rate Qi of the fluid that has passed through the target mesh portion (the inflow-side inner circumferential surface 23) over the short time interval Δt and the concentration (the mass/volume concentration Ds1) of the particulate matter contained in the fluid accumulates at (is collected by) the target mesh portion (the inflow-side inner circumferential surface 23). The CPU 12 then changes the target mesh portion and performs the similar process to derive the thickness Ts of the particulate layer 40 after the short time interval Δt for each of the mesh portions corresponding to the inflow-side inner circumferential surface 23 of the model 21. The values of the thickness Ts of the particulate layer 40 thus derived for the respective mesh portions corresponding to the inflow-side inner circumferential surface 23 represent the distribution of the particulate layer 40 that has accumulated on the inflow-side inner circumferential surface 23. The CPU 12 stores the derived values of the thickness Ts of the particulate layer 40 on the HDD 15 as transient distribution information in association with the respective mesh portions corresponding to the inflow-side inner circumferential surface 23 and the time (the time t+Δt). Note that the analysis is performed in this embodiment on the assumption that all the particulate matter contained in the fluid is collected when the fluid passes through the inflow-side inner circumferential surface 23; however, the assumption is not limited to this one. For example, the distribution of the particulate layer 40 that has accumulated after the short time interval Δt may be derived by taking into account a parameter indicating a collection rate associated with the partition portion 22.

After performing the particulate-layer-distribution deriving process in step S130 in a manner as described above, the CPU 12 increments the time t by the short time interval Δt (step S140) and determines whether the total amount M [kg] of the particulate matter that has accumulated on the inflow-side inner circumferential surface 23 at the time t becomes greater than or equal to the target amount Mg (step S150). That is, the CPU 12 determines whether the total amount M has reached the target amount Mg. Note that the CPU 12 is able to easily derive the total amount M of the particulate matter contained in the particulate layer 40 at each mesh portion on the basis of the thickness Ts of the particulate layer 40 of the mesh portion included in the transient distribution information derived through the immediately preceding particulate layer distribution deriving process, for example. The CPU 12 may store the above-described weights Mi derived for the respective mesh portions corresponding to the inflow-side cell 33 through the immediately preceding particulate-layer-distribution deriving process and may derive the sum of the weights Mi as the total amount M. If the total amount M is not greater than or equal to the target amount Mg, the CPU 12 performs the processing of step S130 and the following steps. That is, the CPU 12 repeatedly performs the particulate-layer-distribution deriving process and a process of incrementing the time t by the short time interval Δt, until the total amount M becomes greater than or equal to the target amount Mg.

When performing the particulate-layer-distribution deriving process for the second or subsequent time, the CPU 12 performs the fluid analysis using the result of the fluid analysis performed in the immediately preceding particulate-layer-distribution deriving process. The CPU 12 performs the fluid analysis also by taking into account the transient distribution information derived through the immediately preceding particulate-layer-distribution deriving process. That is, the CPU 12 performs the fluid analysis for the state where the particulate layer 40 has accumulated on the inflow-side inner circumferential surface 23 as illustrated in FIG. 4. For example, the CPU 12 performs the fluid analysis on the assumption that it becomes more difficult for the fluid to pass through the mesh portion having a larger value of the thickness Ts of the particulate layer 40 among the mesh portions corresponding to the inflow-side inner circumferential surface 23. For example, the CPU 12 derives, for each of the mesh portions corresponding to the inflow-side inner circumferential surface 23, a flow resistance of the particulate layer 40 on the basis of the thickness Ts of the particulate layer 40, the viscosity μ of the fluid, and the permeability αs of the particulate layer 40, and updates the setting condition values (e.g., the flow resistance Ri) of the fluid analysis by taking this result into account. The CPU 12 performs the fluid analysis on the basis of the updated setting condition values. The CPU 12 then derives current transient distribution information, on the basis of the fluid analysis performed by taking into account the transient distribution information derived previous time.

If the total amount M becomes greater than or equal to the target amount Mg in step S150, the CPU 12 derives transient distribution information derived through the last particulate-layer-distribution deriving process as the post-transient-analysis distribution information and stores the post-transient-analysis distribution information on the HDD 15 (step S160). The CPU 12 then ends the transient analysis process, and the routine proceeds to the following step. In this embodiment, the CPU 12 uses the transient distribution information as the post-transient-analysis distribution information without any processing; however, the CPU 12 may use, as the post-transient-analysis distribution information, information obtained by performing processing, such as converting a value included in the transient distribution information. As described above, the CPU 12 repeatedly analyzes a distribution of the accumulated particulate layer 40 after the short time interval Δt (derives the transient distribution information) and derives the post-transient-analysis distribution information that represents the distribution of the accumulated particulate layer 40 when the total amount M has reached the target amount Mg during the transient analysis process. From the viewpoint of the accuracy of the derived post-transient-analysis distribution information, the particulate-layer-distribution deriving process is performed preferably three times or more, more preferably ten times or more, and further more preferably a hundred times or more during the transient analysis process. The number of times the particulate-layer-distribution deriving process is performed during the transient analysis process can be adjusted by appropriately setting the short time interval Δt in accordance with the concentration of the particulate matter in the fluid or the value of the target amount Mg.

After performing the transient analysis process, the CPU 12 performs a fluid analysis based on the object information 19 and the post-transient-analysis distribution information to perform a pressure loss deriving process in which a pressure loss that occurs when the fluid flows inside the honeycomb structure 20 is derived (step S170). Specifically, the CPU 12 performs the fluid analysis by taking into account not only the object information 19 but also the accumulation state (accumulation distribution) of the particulate layer 40 simulated by the post-transient-analysis distribution information to derive a pressure loss (a difference between the pressure at the front end surface 27 and the pressure at the rear end surface 28 of the model 21). This fluid analysis can be performed in a manner similar to the fluid analysis performed during the particulate-layer-distribution deriving process in step S130, for example. For example, the CPU 12 successfully derives a pressure loss on the basis of the absolute pressure Pi at each mesh portion derived through the fluid analysis and the boundary conditions set in step S110. Note that the CPU 12 may perform the pressure loss deriving process by using analysis conditions different from those used in step S130. The CPU 12 stores the derived value of the pressure loss on the HDD 15 as the result of this pressure loss deriving process. Note that each value obtained through the fluid analysis performed during the pressure loss deriving process may be stored on the HDD 15.

If the object information 19 includes information regarding the structure (e.g., information that simulates the structure near the periphery of the honeycomb structure 20) other than the smallest unit (the model 21) of the iterative structure, the CPU 12 may perform the transient analysis process and the pressure loss deriving process also for the structure in a manner similar to the above one. The CPU 12 may derive a pressure loss in the whole honeycomb structure 20 by also taking into account a pressure loss at such a structure different from the smallest unit of the iterative structure.

After performing the pressure loss deriving process, the CPU 12 performs an analysis result output process in which the results of the transient analysis process and the pressure loss analysis process described above are output as analysis result data (step S180). Then, the CPU 12 ends this routine. The analysis result data includes, for example, the post-transient-analysis distribution information and the value of the pressure loss. The analysis result data may also include the transient distribution information at the respective time points from the time point of t=0 to the time point at which the total amount M has become greater than or equal to the target amount Mg. The analysis result data may be output by storing the data on the HDD 15, an external storage medium, or the like or by outputting the analysis results to the display 16 on the basis of the a user instruction received via the input device 17. The pressure loss in the honeycomb structure 20 can be evaluated using this analysis result data in terms of whether the pressure loss in the honeycomb structure 20 is within a permissive range, for example.

Figure 6:
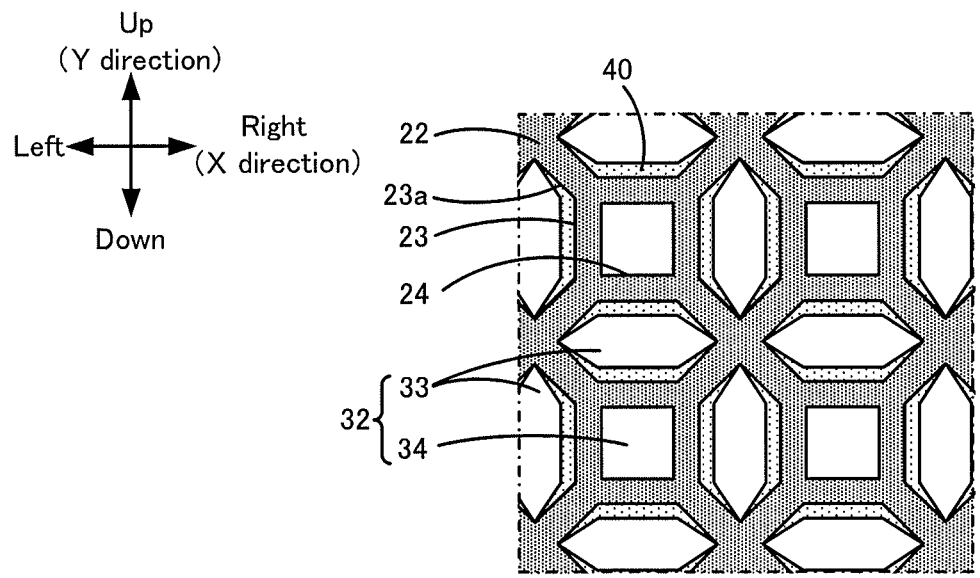
FIG. 6 is a conceptual diagram illustrating an example of an accumulation distribution of a particulate layer 40 represented by post-transient-analysis distribution information.
Figure 7:
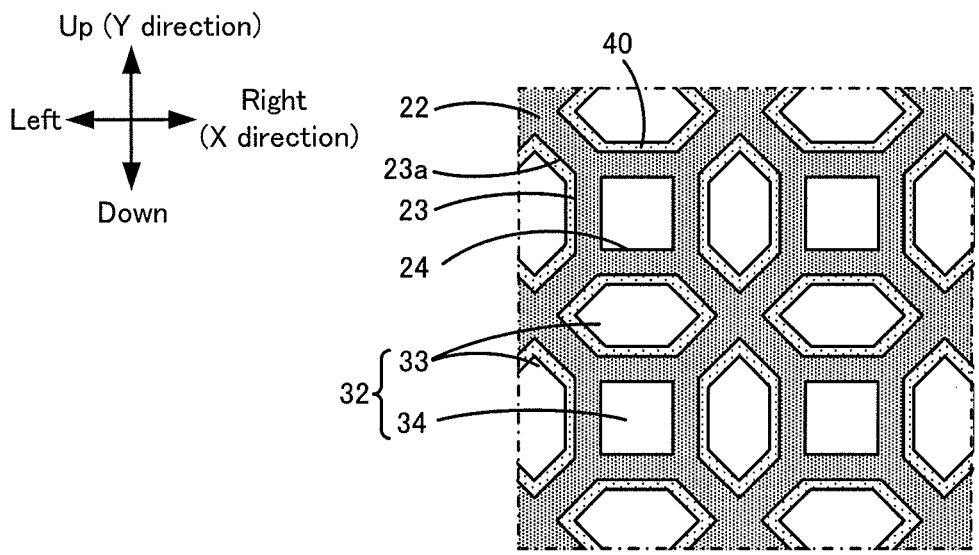
FIG. 7 is a conceptual diagram illustrating an example of a state where the particulate layer 40 is evenly distributed.

Now, the accumulation state of the particulate layer 40 derived through the transient analysis process will be described. FIG. 6 is a conceptual diagram illustrating an example of the accumulation distribution of the particulate layer 40 represented by the post-transient-analysis distribution information. FIG. 7 is a conceptual diagram illustrating an example of a state where the particulate layer 40 is distributed evenly. As described using FIG. 3, the flow of the fluid that has passed through the inflow-inflow facing surface 23*a* of the inflow-side inner circumferential surface 23 differs from that of the fluid that has passed through the other portion of the inflow-side inner circumferential surface 23 in the honeycomb structure 20 according to the embodiment. Specifically, the fluid tends to more easily flow through (the flow resistance is small at) the other portion of the inflow-side inner circumferential surface 23 than at the inflow-inflow facing surface 23*a* of the inflow-side inner circum-ferential surface 23. For this reason, the flow rate of the fluid that passes through the inflow-inflow facing surface 23*a* tends to be small, and consequently the particulate layer 40 is less likely to accumulate on the inflow-inflow facing surface 23*a* (the thickness Ts is less likely to be large). Since the accumulation distribution of the particulate layer 40 after the short time interval Δt is repeatedly analyzed by repeatedly performing the particulate-layer-distribution deriving process in this embodiment, a transient change in the accumulation distribution of the particulate layer 40 over time can be accurately analyzed. Thus, the accumulation state (accumulation distribution) of the particulate layer 40 after the short time interval Δ has passed a plurality of times is accurately simulated by the post-transient-analysis distribution information. That is, the accumulation state of the particulate layer 40 simulated by the derived post-transient-analysis distribution information is uneven as illustrated in FIG. 6, and a relatively small amount of particulate layer 40 has accumulated on the inflow-inflow facing surface 23. It is confirmed that the accumulation distribution of the particulate layer 40 obtained when the fluid actually flows inside the honeycomb structure 20 is similar to the state illustrated in FIG. 6, and the state closer to the actual accumulation state of the particulate layer 40 can be simulated through the transient analysis process according to this embodiment. Since the a pressure loss that occurs when the fluid flows inside the honeycomb structure 20 in this state is derived in the analysis process according to this embodiment, the pressure loss can be analyzed by more accurately simulating the accumulation state of the particulate matter. As a method for simulating the state of the particulate layer 40 without performing the transient analysis process, the state where the particulate layer 40 has accumulated evenly at every position on the inflow-side inner circumferential surface 23 as illustrated in FIG. 7 (the state where the particulate layer 40 is distributed evenly) may be simulated. However, since this state differs from the actual accumulation state of the particulate layer 40, a deviation from the actually measured value tends to be large when the pressure loss is analyzed in this state, and the analysis accuracy tends to decrease.

FIG. 6 illustrates an example of the accumulation distribution of the particulate layer 40 on a cross-section perpendicular to the front-rear direction of the honeycomb structure 20; however, the accumulation state of the particulate layer 40 may be uneven also depending on the position in the front-rear direction of the honeycomb structure 20. The post-transient-analysis distribution information determined through the transient analysis process according to this embodiment is information also simulating such an accumulation distribution in the front-rear direction.

Now, correspondences each between an element of this embodiment and an element of an aspect of the present invention will be clarified. The analysis apparatus 10 according to this embodiment corresponds to a pressure loss analysis apparatus according to an aspect of the present invention. The CPU 12 corresponds to transient analysis device and pressure loss deriving device. Note that this embodiment also discloses an example of a pressure loss analysis method and an example of a program for executing the pressure loss analysis method according to aspects of the present invention by describing the operation of the analysis apparatus 10.

According to the analysis apparatus 10 according to this embodiment described in detail above, the CPU 12 derives transient distribution information that represents an accumulation distribution of the particulate layer 40 on the inflow-side inner circumferential surface 23 of the honeycomb structure 20 (the model 21) at a time point after the short time interval Δt by performing a fluid analysis. The CPU 12 then repeatedly derives transient distribution information by performing a fluid analysis while taking into account the transient distribution information derived previous time, and consequently derives post-transient-analysis distribution information that represents the accumulation distribution of the particulate layer 40 at a later time point. By repeatedly analyzing the distribution of the accumulated particulate layer 40 at each time point after the short time interval Δt in this way, a transient change in the accumulation distribution of the particulate layer 40 over time can be accurately analyzed. Thus, the accumulation state (accumulation distribution) of the particulate layer 40 at a time point after the short time interval Δt has passed a plurality of times is accurately simulated by the post-transient-analysis distribution information. For example, the state closer to the actual accumulation state of the particulate layer 40 can be simulated compared with the case of simulating a state where the particulate layer 40 has accumulated evenly at every position on the inflow-side inner circumferential surface 23 (state where the particulate layer 40 is distributed evenly). Since a pressure loss for the case where the fluid flows inside the honeycomb structure 20 is derived on the basis of this post-transient-analysis distribution information, the pressure loss can be analyzed by more accurately simulating the accumulation state of the particulate matter.

In addition, during a particulate-layer-distribution deriving process, the CPU 12 derives the transient distribution information on the basis of information regarding a concentration of the particulate matter in the fluid (mass/volume concentration Ds1) and information regarding a flow rate of the fluid that flows into each of the mesh portions corresponding to the inflow-side inner circumferential surface 23 (flow rate Qi), information regarding a flow rate being a value derived through the fluid analysis performed during the particulate-layer-distribution deriving process. Here, the higher the concentration of the particulate matter in the fluid and the larger the flow rate of the fluid that flows through the inflow-side inner circumferential surface 23, the more the particulate matter accumulates. Accordingly, the transient distribution information can be appropriately derived by using the information regarding the concentration of the particulate matter in the fluid and the information regarding the flow rate of the fluid. That is, the accumulation state of the particulate layer 40 can be appropriately simulated.

Further, each of the transient distribution information and the post-transient-analysis distribution information is information including at least one of a distribution of the thickness Ts of the particulate layer 40, a distribution of permeability of the particulate layer 40, and a distribution of flow resistance of the particulate layer 40. More specifically, each of the transient distribution information and the post-transient-analysis distribution information is information including a distribution of the thickness Ts of the particulate layer 40. Since the thickness Ts is information that influences a pressure loss that occurs when the fluid passes through the particulate layer 40, it is suitable as information representing the accumulation distribution of the particulate layer 40 (the transient distribution information and the post-transient-analysis distribution information).

Furthermore, during the transient analysis process, the CPU 12 repeatedly performs the particulate-layer-distribution deriving process until the total amount M of the particulate matter that has accumulated on the inflow-side inner circumferential surface 23 reaches the predetermined target amount Mg. Accordingly, the accumulation state of the particulate layer 40 in a state for which analysis of the pressure loss is desired (state where the target amount Mg has been reached) can be simulated relatively easily, and the pressure loss in that state can be derived easily.

The object information 19 is information that simulates the honeycomb structure 20 having the area ratio A of 15% or greater, the area ratio A being a ratio of the inflow-inflow facing area to an area of the inflow-side inner circumferential surface 23, the inflow-inflow facing area being an area of a portion (the inflow-inflow facing surface 23a) of the inflow-side inner circumferential surface 23 facing the inflow-side inner circumferential surface 23 of another inflow-side cell 33. When a fluid containing particulate matter passes through the honeycomb structure 20, the particulate matter is unlikely to accumulate evenly on the inflow-side inner circumferential surface 23 in the honeycomb structure 20 having the area ratio A of 15% or greater. Accordingly, the value of the pressure loss derived by simulating the state where the particulate layer 40 is distributed evenly tends to deviate from the actually measured value of the pressure loss measured using the honeycomb structure 20 in which the same amount of particulate matter has accumulated. That is, the accuracy of the pressure loss analysis tends to decrease. In contrast, a deviation of the value derived through the analysis process according to the above-described embodiment from the actually measured value is small also for the honeycomb structure 20 having the area ratio A of 15% or greater, and thus the pressure loss analysis can be performed more accurately. Therefore, it is beneficial to employ the present invention when the pressure loss analysis is performed for the honeycomb structure 20 having the area ratio A of 15% or greater.

The present invention is by no means limited to the embodiments described above, and can be carried out in various ways within the technical scope of the present invention.

For example, it is assumed in the above-described embodiment that the honeycomb structure 20 has the shape illustrated in FIGS. 2 and 3; however, the shape is not limited to this one. Whatever shape the honeycomb structure has, a pressure loss can be analyzed by more accurately simulating the accumulation state of the particulate matter by using object information that simulates the honeycomb structure, as in the embodiment described above. FIGS. 8 to 14 are cross-sectional diagrams illustrating the cell structure (positional relationships between the inflow-side cells 33 and the outflow-side cells 34) in honeycomb structures according to modifications. In FIGS. 8 to 14, the outflow-side cells 34 are hatched so as to be easily distinguished from the others. For example, the cross-sectional shape of the cells 32 can be polygonal such as triangular, quadrangular (e.g., FIGS. 8 to 10 and 12 to 14), hexagonal (e.g., FIG. 11), or octagonal (e.g., FIGS. 9 and 10); circular; or elliptical. The inflow-side cells 33 and the outflow-side cells 34 have different shapes in the above-described embodiment; however, they may have the same shape (e.g., FIGS. 8 and 11). In addition, the plurality of inflow-side cells 33 have the same shape and the plurality of outflow-side cells 34 have the same shape in the above-described embodiment; however, at least the inflow-side cells 33 or the outflow-side cells 34 may have two or more shapes (e.g., FIGS. 10 and 12). For example, the inflow-side cells 33 illustrated in FIG. 10 have two cross-sectional shapes, i.e., quadrangular and octagonal shapes. The inflow-side cells 33 illustrated in FIG. 12 have two cross-sectional shapes, i.e., square and rectangular shapes. In addition, the honeycomb structure 20 structured such that the inflow-side cells 33 and the outflow-side cells 34 described in the above-described embodiment and FIGS. 8 to 14 are arranged oppositely may be employed. In addition, the inflow-side cells 33 are plugged with the rear-side plugging portion 38 and the outflow-side cells 34 are plugged with the front-side plugging portion 37 in the above-described embodiment; however, the configuration is not limited to this one. For example, the inflow-side cells 33 need not be plugged with the rear-side plugging portion 38.

It is assumed in the above-described embodiment that the object information 19 is information that simulates the honeycomb structure 20 having the area ratio A of 15% or greater; however, the object information 19 is not limited to this one. Even when an analysis is performed on the basis of the object information 19 that simulates the honeycomb structure 20 having the area ratio A greater than or equal to 0% and less than 15%, a pressure loss can be analyzed by more accurately simulating the accumulation state of the particulate matter as in the above-described embodiment. However, since the value of the pressure loss derived by simulating the state where the particulate layer 40 is evenly distributed without performing the transient analysis process tends to deviate from the actual measured value as the value of the area ratio A becomes larger, particularly, the area ratio A becomes larger than or equal to 15%, it is beneficial to employ the present invention. Although the upper limit of the area ratio A is 100%, the area ratio A of the honeycomb structure is practically less than or equal to 90%, for example.

The particulate-layer-distribution deriving process is repeatedly performed during the transient analysis process until the total amount M of the particulate matter that has accumulated on the inflow-side inner circumferential surface 23 reaches the predetermined target amount Mg in the above-described embodiment; however, the configuration is not limited to this one. For example, the CPU 12 may repeatedly perform the particulate-layer-distribution deriving process until the sum of the short time intervals Δt reaches a predetermined target period tg [s]. With this configuration, the accumulation state of the particulate layer 40 in a state for which analysis of the pressure loss is desired (state the target period tg has been reached) can be simulated relatively easily, and a pressure loss in that state can be derived easily. In addition, the CPU 12 may repeatedly perform the particulate-layer-distribution deriving process until at least one of the total amount M of the particulate matter reaches the predetermined target amount Mg or the sum of the short time intervals Δt reaches the predetermined target period tg. In addition, the total amount M and the target amount Mg are represented by weight [kg] in the above-described embodiment; however, they may be represented as a weight of particulate matter per unit volume of the honeycomb structure (the model 21) [g/L] or a volume [m$^3$] of the particulate matter. Alternatively, the CPU 12 may repeatedly perform the particulate-layer-distribution deriving process until it receives an end instruction from the user.

Each of the transient distribution information and the post-transient-analysis distribution information is information including a distribution of the thickness Ts of the particulate layer 40 in the above-described embodiment; however, the information is not limited to this one. Each of the transient distribution information and the post-transient-analysis distribution information may be information including at least one of the distribution of thickness of the particulate layer 40, the distribution of permeability of the particulate layer 40, and the distribution of flow resistance of the particulate layer 40. Since the permeability and the flow resistance of the particulate layer 40 as well as the thickness are information that influences the pressure loss that occurs when the fluid passes through the particulate layer 40, they are suitably used as the information representing the accumulation distribution of the particulate layer 40 (the transient distribution information and the post-transient-analysis distribution information). In the case where each of the transient distribution information and the post-transient-analysis distribution information is information including the distribution of permeability of the particulate layer 40, for example, the value of the permeability αs [μm$^2$] of the particulate layer 40 may be derived for each of the mesh portions corresponding to the inflow-side inner circumferential surface 23 during the particulate-layer-distribution deriving process in step S130 by setting the thickness of the particulate layer 40 to be constant (does not change over time) for all the mesh portions corresponding to the inflow-side inner circumferential surface 23 by using the physical property conditions of the particulate layer 40. In addition, any other information may be used as the transient distribution information and the post-transient-analysis distribution information if the information is capable of simulating the accumulation state (accumulation distribution) of the particulate layer 40.

The CPU 12 derives the transient distribution information during the particulate-layer-distribution deriving process on the basis of the concentration (mass/volume concentration Ds1) of the particulate matter in the fluid and the flow rate Qi of the fluid that flows into each of the mesh portions corresponding to the inflow-side inner circumferential surface 23, the flow rate Qi being a value derived through the fluid analysis performed during the particulate-layer-distribution deriving process, in the above-described embodiment; however, the configuration is not limited to this one. The transient distribution information may be derived on the basis of any information regarding the concentration of the particulate matter in the fluid (e.g., information convertible into the concentration, information from which the concentration can be derived, information equivalent to the concentration, etc.) and any information regarding the flow rate of the fluid that flows into each of the mesh portions corresponding to the inflow-side inner circumferential surface 23 (e.g., information convertible into the flow rate, information from which the flow rate can be derived, or information equivalent to the flow rate). For example, the volume concentration Ds2 [vol%] may be used as the information regarding the concentration. For example, a flow velocity Vi of the fluid that flows from a mesh portion corresponding to the adjacent inflow-side cell 33 to the mesh portion corresponding to the inflow-side inner circumferential surface 23 may be used as the information regarding the flow rate. Alternatively, any other value may be used as long as the transient distribution information can be derived based on the fluid analysis.

The object information 19 may simulate the honeycomb structure in which the partition portions 22 include a collection layer in the above-described embodiment. Specifically, the honeycomb structure 20 illustrated in FIGS. 2 and 3 may include the partition portions 22 each including a partition wall (corresponding to the partition portion 22 in the above-described embodiment) and a collection layer. In this case, mesh portions corresponding to the partition portions 22 may be further classified into mesh portions corresponding to the partition wall and mesh portions corresponding to the collection layer in the object information 19. The object information 19 may also include information regarding permeability of the partition wall (equivalent to the permeability αw [μm$^2$] in the above-described embodiment) and information regarding permeability of the collection layer. When the partition portion 22 includes a collection layer, the surface of the collection layer serves as the inflow-side inner circumferential surface 23.

The pressure loss value predicted for the state where the predetermined total amount M of particulate matter has accumulated is derived by performing the pressure loss deriving process in step S170 after performing the transient analysis process in the above-described embodiment; however, the configuration is not limited to this one. For example, a relationship between the total amount M of particulate matter and the pressure loss may be derived a plurality of times from a state where the total amount M is equal to 0 to a state where the total amount M is equal to the final accumulation amount (e.g., the target amount Mg). For example, the CPU 12 can derive the pressure loss on the basis of the absolute pressure Pi at each mesh portion derived in an n-th particulate-layer-distribution deriving process performed during the transient analysis process as in the pressure loss deriving process performed in step S170. The resultant pressure loss is a value taking into account the transient distribution information derived through an (n−1)-th particulate-layer-distribution deriving process and corresponds to a pressure loss for the accumulation state of the particulate layer 40 represented by the (n−1)-th transient distribution information. Accordingly, the CPU 12 may store the pressure loss derived through the n-th particulate-layer-distribution deriving process in association with the total amount M based on the transient distribution information derived in the (n−1)-th particulate-layer-distribution deriving process (i.e., the total amount M obtained in step S150 performed for the (n−1)-th time) on the HDD 15 every time the CPU 12 performs the particulate-layer-distribution deriving process. In addition, the CPU 12 may include such a correspondence between the pressure loss and the total amount M in the analysis result data output in step S180. In this way, the user can grasp not only the ultimate pressure loss derived in step S170 but also the pressure loss during accumulation of the particulate layer 40 and a change in the pressure loss.

The CPU 12 uses a product of the concentration (mass/volume concentration Ds1) of particulate matter in the fluid, the flow rate Qi of the fluid that flows into each of the mesh portions corresponding to the inflow-side inner circumferential surface 23, and the short time interval $\Delta t$ as the weight Mi of the accumulated particulate matter when deriving the transient distribution information; however, the configuration is not limited to this one. For example, a value obtained by multiplying "Ds1×Qi×$\Delta t$" by a calculation acceleration factor Ac may be used as the weight Mi (where Ac>1). In this way, the mass/volume concentration Ds1 can be made Ac times as large as the actual value (value for the fluid used for simulation), and the calculation can be performed by increasing the amount of particulate matter that accumulates over the short time interval $\Delta t$. Accordingly, the number of times the particulate-layer-distribution deriving process is performed during the transient analysis process until the total amount M reaches the target amount Mg can be reduced, and consequently time taken for the transient analysis process can be reduced. For example, when the value of the mass/volume concentration Ds1 is very small, formation of the particulate layer 40 takes time, which may require the particulate-layer-distribution deriving process to be repeatedly performed many times during the transient analysis process until the total amount M reaches the target amount Mg, and consequently, the calculation may take long. In such a case, the use of the calculation acceleration factor Ac can reduce the time taken for the transient analysis process. Note that when the calculation acceleration factor Ac is used, the product of the short time interval $\Delta t$ and the calculation acceleration factor Ac can be construed as the time in reality. For example, when the particulate-layer-distribution deriving process is repeatedly performed n times during the transient analysis process, the analysis is performed from a time point of t=0 to a time point of t=n×$\Delta t$. This can be construed as the analysis being performed from a time point of $t_R$=0 to a time point of $T_R$=n×$\Delta t$×Ac in reality. The time period and the time point included in the analysis result data output in step S180 may be the time period and the time point $t_R$ obtained by such a conversion.

EXAMPLES

The case where the analysis process program and the pressure loss analysis apparatus described above were actually created will be described as an example below. Note that the present invention is not limited to the example below.

Example and Comparative Example

As an example, an analysis process program implementing the functions according to the above-described embodiment was created. This program was stored on an HDD of a computer including the HDD and a controller including a CPU, a ROM, and a RAM, whereby a pressure loss analysis apparatus according to the example was created. In addition, an analysis process program for performing the pressure loss deriving process of step S170 without performing the transient analysis process illustrated in FIG. 5 was stored on an HDD of a computer, whereby a pressure loss analysis apparatus according to a comparative example was created.

[Pressure Loss Analysis of Honeycomb Structures 1 to 4]

Figure 8:
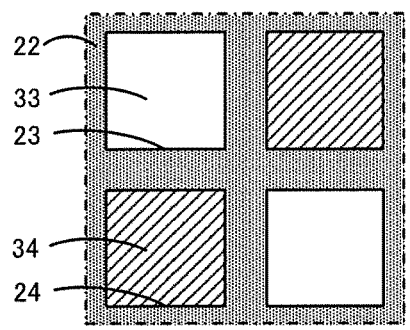
FIG. 8 is a cross-sectional diagram illustrating inflow-side cells 33 and outflow-side cells 34 of a honeycomb structure according to a modification.
Figure 9:
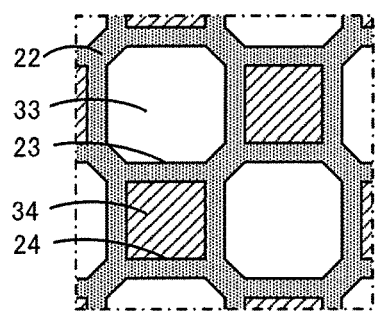
FIG. 9 is a cross-sectional diagram illustrating inflow-side cells 33 and outflow-side cells 34 of a honeycomb structure according to a modification.
Figure 10:
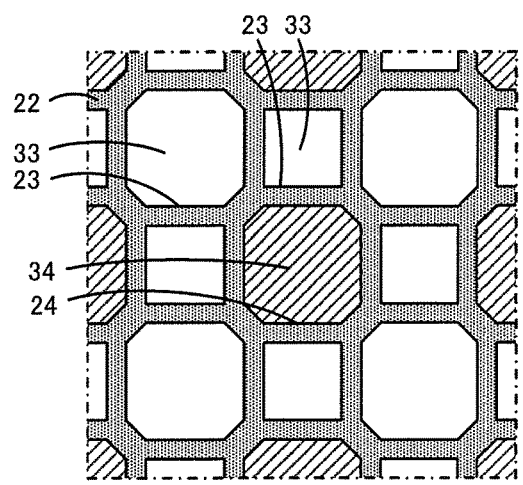
FIG. 10 is a cross-sectional diagram of a cell structure of a honeycomb structure according to a modification.
Figure 11:
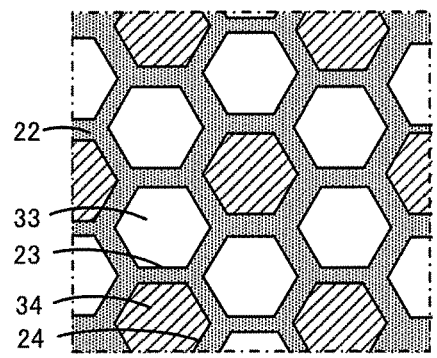
FIG. 11 is a cross-sectional diagram of a cell structure of a honeycomb structure according to a modification.
Figure 12:
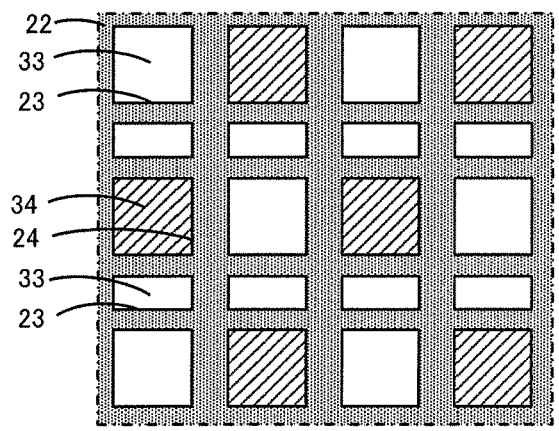
FIG. 12 is a cross-sectional diagram of a cell structure of a honeycomb structure according to a modification.
Figure 13:
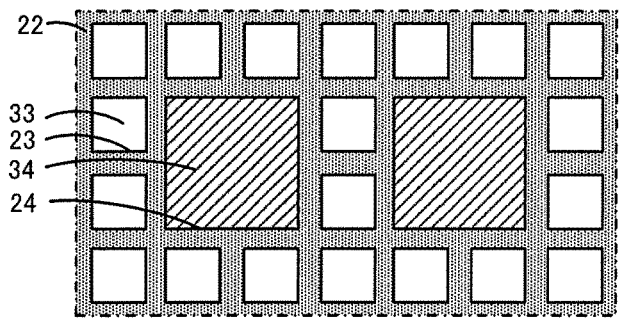
FIG. 13 is a cross-sectional diagram of a cell structure of a honeycomb structure according to a modification.
Figure 14:
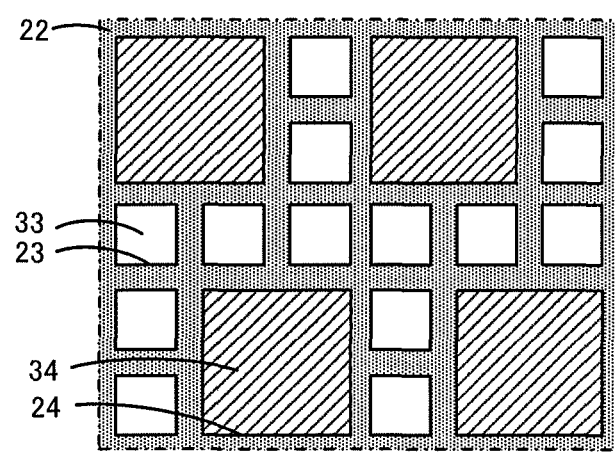
FIG. 14 is a cross-sectional diagram of a cell structure of a honeycomb structure according to a modification.

Object information simulating each of honeycomb structures 1 to 4 was created. The pressure loss analysis apparatuses according to the example and the comparative example were caused to execute the respective analysis process programs on the basis of this object information to derive the pressure loss. The honeycomb structure 1 is structured such that both the inflow-side cells 33 and the outflow-side cells 34 have quadrangular cross-sectional shapes and are alternately arranged as illustrated in FIG. 8. Since the honeycomb structure 1 does not have the inflow-inflow facing surface 23a, its area ratio A is 0%. The honeycomb structure 2 is structured such that the inflow-side cells 33 have an octagonal shape and the outflow-side cells 34 have a quadrangular shape and are alternately arranged as illustrated in FIG. 9. In the honeycomb structure 2, four sides inclined from the up-down and right-left directions of the octagonal shape of the inflow-side cells 33 illustrated in FIG. 9 serve as the inflow-inflow facing surface 23a, and thus its area ratio A is 10%. The honeycomb structure 3 is structured in the same manner as the honeycomb structure 2 except for the area ratio A, which is 15%. The honeycomb structure 4 is structured as illustrated in FIGS. 2 and 3, and its area ratio A is 63%. In addition, in the example, the transient analysis process was performed until the total amount M [g/L] of particulate matter per unit volume of the honeycomb structure (the model 21) has reached the target amount Mg (=4 g/L). In the example, the particulate-layer-distribution deriving process was performed 200 times (until the total amount M has reached the target amount Mg). In the comparative example, the pressure loss was derived using object information simulating the state where the target amount Mg (=4 g/L) of particulate matter (the particulate layer 40) has evenly accumulated in the inflow-side cells 33. In addition, the honeycomb structures 1 to 4 were actually produced, and values of the pressure loss that occurs when the fluid passes were measured in the following manner. First, the honeycomb structures 1 to 4 having a diameter of 144 mm and a length of 152 mm were produced by joining together 16 plugged honeycomb structure segments (having a quadrangular cylindrical shape of a 36 mm×36 mm quadrangle and a length of 152 mm) composed of porous Si-bond SiC (Si—SiC) and by processing the periphery of the resultant structure. The honeycomb structures 1 to 4 were installed in an exhaust system of a 2.0 L diesel engine, and the diesel engine was operated at conditions of an engine speed of 2000 rpm, an engine torque of 60 Nm, an exhaust temperature of 250° C., and an exhaust flow rate of 2.5 m³/min. The pressure loss was measured when 4g/L of particulate matter (such as soot) has accumulated. Then, an error (%) of the derived pressure loss from the actually measured value was derived for each of the example and the comparative example.

Table 1 collectively shows the structures of the cells and the area ratio A of the honeycomb structures 1 to 4, the error in the comparative example from the actually measured value, and the error in the example from the actually measured value. As shown in Table 1, the error in the example was smaller than or equal to the error in the comparative example for all of the honeycomb structures 1 to 4. In addition, the error of the pressure loss derived in the comparative example for the honeycomb structures 3 and 4 having the area ratio A of 15% or greater from the actually measured value was greater than or equal to 15%, which was large and exceeded the permissible margin of error. In contrast, in the example, the error for the honeycomb structures 3 and 4 was substantially the same as that for the honeycomb structures 1 and 2 and was within the permissive range.

information that represents an accumulation distribution of a particulate layer on an inflow-side inner circumferential surface is derived by performing a fluid analysis for the case where the fluid flows inside the honeycomb structure on the basis of object information that simulates the honeycomb structure with a plurality of mesh portions and by deriving, for each of the mesh portions corresponding to the inflow-side inner circumferential surface that is an inner circumferential surface of each of the inflow-side cells among a surface of the partition portion, a state of the particulate layer, which is a layer in which particulate matter contained in the fluid has accumulated, at a time point after a short time interval, and of deriving post-transient-analysis distribution information that represents the accumulation distribution at a time point after the particulate-layer-distribution deriving process has been performed a plurality of times, by performing the fluid analysis during the particulate-layer-distribution deriving process performed for the second and following times while taking into account the transient distribution information derived in an immediately preceding particulate-layer-distribution deriving process; and a pressure loss deriving step, in the pressure loss deriving device, of deriving a pressure loss for the case where the fluid flows inside the honeycomb structure, by performing a fluid analysis on the basis of the object information and the post-transient-analysis distribution information, wherein the pressure loss derived in the pressure loss deriving step is used to evaluate a honeycomb structure.

2. The pressure loss analysis method according to claim 1, wherein during the particulate-layer-distribution deriving process, the transient distribution information is derived on the basis of information regarding a con-

TABLE 1

| | Structure of cell | | | Error from actually measured value of pressure loss [%] | |
|---|---|---|---|---|---|
| | Cross-sectional shape of inflow-side cell | Cross-sectional shape of outflow-side cell | Area ratio A [%] | Comparative example | Example |
| Honeycomb structure 1 | Quadrangular | Quadrangular | 0 | 2 | 2 |
| Honeycomb structure 2 | Octagonal | Quadrangular | 10 | 3 | 3 |
| Honeycomb structure 3 | Octagonal | Quadrangular | 15 | 15 | 3 |
| Honeycomb structure 4 | Hexagonal | Quadrangular | 63 | 30 | 3 |

The present application claims priority of Japanese Patent Application No. 2015-202114 filed on Oct. 13, 2015, the entire contents of which are incorporated herein by reference.

What is claimed is:

1. A pressure loss analysis method for analyzing a pressure loss in a honeycomb structure for a case where a fluid flows inside the honeycomb structure, the honeycomb structure including porous partition portions that form a plurality of inflow-side cells and a plurality of outflow-side cells using a pressure loss analysis apparatus comprising: a computing apparatus, which includes a transient analysis device and a pressure loss deriving device:

the pressure loss analysis method comprising:

a transient analysis step, in the transient analysis device, of repeatedly performing a particulate-layer-distribution deriving process, in which transient distribution centration of the particulate matter in the fluid and information regarding a flow rate of the fluid that flows into each of the mesh portions corresponding to the inflow-side inner circumferential surface, the information regarding a flow rate being a value derived through the fluid analysis performed during the particulate-layer-distribution deriving process.

3. The pressure loss analysis method according to claim 1, wherein each of the transient distribution information and the post-transient-analysis distribution information is information including at least one of a distribution of thickness of the particulate layer, a distribution of permeability of the particulate layer, and a distribution of flow resistance of the particulate layer.

4. The pressure loss analysis method according to claim 1, wherein in the transient analysis step, the particulate-layer-distribution deriving process is performed repeatedly until at least one of a total amount of the particulate matter that has accumulated on the inflow-side inner circumferential surface reaches a predetermined target amount or the sum of the short time intervals reaches a predetermined target period.

5. The pressure loss analysis method according to claim 1, wherein the object information is information that simulates the honeycomb structure having an area ratio A of 15% or greater, the area ratio A being a ratio of an inflow-inflow facing area to an area of the inflow-side inner circumferential surface, the inflow-inflow facing area being an area of a portion of the inflow-side inner circumferential surface that faces the inflow-side inner circumferential surface of another inflow-side cell.

6. A non-transitory computer readable recording medium storing a program that, upon execution of which by one or a plurality of computers, performs the individual steps of the pressure loss analysis method according to claim 1.

7. A pressure loss analysis apparatus for analyzing a pressure loss in a honeycomb structure for a case where a fluid flows inside the honeycomb structure, the honeycomb structure including porous partition portions that form a plurality of inflow-side cells and a plurality of outflow-side cells, the pressure loss analysis apparatus comprising:
 a computing apparatus including:
 a transient analysis device for repeatedly performing a particulate-layer-distribution deriving process, in which transient distribution information that represents an accumulation distribution of a particulate layer on an inflow-side inner circumferential surface is derived by performing a fluid analysis for the case where the fluid flows inside the honeycomb structure on the basis of object information that simulates the honeycomb structure with a plurality of mesh portions and by deriving, for each of the mesh portions corresponding to the inflow-side inner circumferential surface that is an inner circumferential surface of each of the inflow-side cells among a surface of the partition portion, a state of the particulate layer, which is a layer in which particulate matter contained in the fluid has accumulated, at a time point after a short time interval, and for deriving post-transient-analysis distribution information that represents the accumulation distribution at a time point after the particulate-layer-distribution deriving process has been performed a plurality of times, by performing the fluid analysis during the particulate-layer-distribution deriving process performed for the second and following times while taking into account the transient distribution information derived in an immediately preceding particulate-layer-distribution deriving process; and
a pressure loss deriving device for deriving a pressure loss for the case where the fluid flows inside the honeycomb structure, by performing a fluid analysis on the basis of the object information and the post-transient-analysis distribution information,
wherein the pressure loss derived by the pressure loss deriving device is used to evaluate a honeycomb structure.

\* \* \* \* \*